(12) United States Patent
Rajapurkar et al.

(10) Patent No.: US 7,927,880 B2
(45) Date of Patent: Apr. 19, 2011

(54) METHODS AND KIT FOR EARLY DETECTION OF ACUTE CORONARY SYNDROME AND PREDICTION OF ADVERSE CARDIAC EVENTS

(76) Inventors: Mohan Rajapurkar, Nadiad (IN); Suhas Lele, Baroda (IN); Sudhir Shah, Arkansas, AR (US)

(*) Notice: Subject to any disclaimer, the term of this patent is extended or adjusted under 35 U.S.C. 154(b) by 21 days.

(21) Appl. No.: 12/124,185

(22) Filed: May 21, 2008

(65) Prior Publication Data

US 2009/0291985 A1 Nov. 26, 2009

(51) Int. Cl.
*G01N 33/20* (2006.01)
(52) U.S. Cl. ......... 436/84; 436/161; 436/164; 436/514; 436/528; 436/530; 436/807; 436/808; 436/810; 436/811; 422/56; 422/58; 422/60; 422/61; 435/7.4; 435/7.94; 435/970; 435/973; 435/975
(58) Field of Classification Search .............. 436/84, 436/514, 528, 530, 531, 161, 164, 807, 808, 436/810, 811; 422/56, 58, 60, 61; 435/7.4, 435/7.94, 970, 973, 975
See application file for complete search history.

(56) References Cited

U.S. PATENT DOCUMENTS
5,744,358 A 4/1998 Jackowski

FOREIGN PATENT DOCUMENTS
| WO | WO9604552 | 2/1996 |
|---|---|---|
| WO | WO02089657 | 11/2002 |
| WO | WO2007005426 | 1/2007 |

OTHER PUBLICATIONS

Pincemail J, et al. Evaluating an individual's oxidative stress: a reality for doctors, online Jan. 27, 2006. retreived from internet site: http://web.archive.org/web/20060127012846/http://www.probiox.com/de/html/documents/EvaluatingOxidativeStress_000.PDF.*
Gutteridge, John M., et al. Transient iron overload with bleomycin detectable iron in the plasma of patients with adult respiratory distress syndrome, 1994, Thorax, vol. 49, pp. 707-710.*
Sempos, C.T. Body iron stores and the risk of coronary heart disease, The New England journal of medicine Apr. 1994, vol. 330, No. 16, pp. 1119 and 1124, ISSN 0028-4793.

* cited by examiner

*Primary Examiner* — Yelena G Gakh
*Assistant Examiner* — Robert Xu
(74) *Attorney, Agent, or Firm* — Hamilton, Brook, Smith & Reynolds, P.C.

(57) ABSTRACT

The invention provides methods for early diagnosis or detection of acute coronary syndrome and prediction of adverse cardiac events on the basis of elevations of catalytic iron in biological fluid of a human subject. An embodiment of the invention provides a method for early detection of acute coronary syndrome (ACS) in a human subject at the time of presentation of the chest pain. The method includes analyzing a test sample of the biological fluid for amount of catalytic iron and detecting acute coronary syndrome in the human subject.

9 Claims, 4 Drawing Sheets

| sBDI (UNITS) | SENSITIVITY | SPECIFICITY | POSITIVE PREDICTIVE VALUE | NEGATIVE PREDICTIVE VALUE | ACCURACY |
|---|---|---|---|---|---|
| 0.10 | 100 (100-100) | 44 (39-48) | 53 (48-58) | 100 (100-100) | 66 (61-70) |
| 0.20 | 93 (90-95) | 88 (85-91) | 77 (73-81) | 97 (95-98) | 90 (87-93) |
| __0.30__ | __84 (81-88)__ | __95 (93-97)__ | __87 (84-90)__ | __93 (91-96)__ | __92 (89-94)__ |
| 0.40 | 75 (71-79) | 98 (96-99) | 93 (91-96) | 90 (87-93) | 91 (88-94) |
| 0.50 | 67 (62-71) | 99 (98-100) | 97 (95-98) | 88 (85-91) | 89 (87-92) |
| 0.60 | 61 (57-66) | 99 (99-100) | 98 (96-99) | 86 (83-89) | 88 (85-91) |

METHODS AND KIT FOR EARLY DETECTION OF ACUTE CORONARY SYNDROME AND PREDICTION OF ADVERSE CARDIAC EVENTS

RELATED APPLICATIONS

Benefit is claimed under 35 U.S.C. 119(a)-(d) to Foreign Indian application Ser No. 455/MUM/2008 entitled "BIOMAKER FOR EARLY DIAGNOSIS OF ACUTE CORONARY SYNDROME AND PREDICTION OF ADVERSE CARDIAC EVENT IN", filed on 5 Mar. 2008, which is herein incorporated in its entirety by reference for all purposes.

FIELD OF INVENTION

The invention relates to methods for early detection of heart diseases. More particularly the invention relates to methods for early detection of acute coronary syndrome and prediction of adverse cardiac outcomes, by detecting and analyzing the amount of catalytic iron in blood, serum or plasma sample of a human subject.

BACKGROUND

Patients presenting with chest pain pose major diagnostic and therapeutic challenges. One of the challenge is to determine if the cause of the chest pain is something benign like muscular pain or it is because of arterial blockage leading to obstruction in blood supply and hence death of heart muscle. The Electrocardiogram (ECG) test is helpful in certain cases if there is clear-cut evidence of heart attack. However, ECG test may not be very helpful in a vast majority of cases in separating the muscular pain from the more dangerous cardiac pain. In such cases diagnosis and treatment becomes difficult for patients with a suspected heart disease e.g. who have non-diagnostic electrocardiograms.

For most emergency physicians it is desirable to have a highly sensitive and highly specific test for detection of acute coronary syndrome for making diagnostic and therapeutic decisions at the right time, particularly within a relatively short period of time following the onset of chest pain. Various serum markers such as creatine Kinase (CK) and its more cardiac specific isoenzymes (CK-MB) were used for diagnosis of acute myocardial infarction. CK-MB has been a preferred marker for many years due to high specificity for cardiac tissues of MB fraction of CK. However, false positive results may occur due to presence of e.g. CK-MB released from skeletal muscle, myopathies, hypothyroidism etc. A reported disadvantage of the CK-MB is delayed diagnosis and poor prognostic index. A pattern of rise and fall may take about 10-30 hours, requiring serial determinations over a period of 24 hours. Marker such as cardiac Troponin T and I are highly specific for cardiac problems e.g. myocardial injury. These proteins are not present in smooth muscle and in the blood of normal healthy human subjects. For the purpose of diagnosis, the problem of false positives has been reported with Troponin. Troponins may be helpful for patients in which CK-MB is elevated due to release from skeletal muscle. It is also reported in the literature that elevated serum plasma Troponins provide useful prognostic information. Elevated levels of either cTnT or cTnI may indicate a much higher chances of adverse cardiac outcomes. Across the acute coronary syndrome spectrum, patients with ST elevation myocardial infarction are the easiest to identify and hence early management strategies are well defined. Non ST elevation myocardial infarction patients also benefit from early invasive strategies but the intervention is usually delayed up to 24 hours due largely in part because of the absence of a predictable early biomarker in the setting of non-diagnostic electrocardiogram. Some of the studies suggests that Troponins are useful for the evaluation of patients with chest pain in the emergency department (ED), however they may not be utilized as a sole criteria e.g. in cases with negative Troponin values especially when a patient presents early after onset of chest pain.

Over the years, cardiac biomarkers have been evaluated for multiple clinical purposes such as screening for preclinical disease, diagnosis of disease in patients with nonspecific symptoms and non-diagnostic electrocardiograms, risk stratification in patients with clinical disease and as a guide in selection of appropriated therapeutic options. The commonly used biomarker called Troponin I or Troponin T both detect death of heart muscle or myonecrosis. The test however comes positive six to twelve hours after the onset of the pain even if there is muscle necrosis. Thus, from the time of onset of chest pain for up to six hours there is no reliable way of separating cardiac chest pain from non-cardiac chest pain. In such situations patients are admitted and observed as if they have a heart attack until a more accurate assessment may be made at e.g. twelve hours. Thus, not only is the diagnosis delayed adding to hospital costs but important treatments like dual anti-platelet therapy and angioplasty are also delayed until a correct diagnosis may be established. Diagnostic tests have been developed to determine whether or not the source of the chest pain is cardiac or whether the human subject has suffered some heart problem e.g. a myocardial infarct or unstable angina. However, these tests do not provide sufficient information for an early detection of ACS and information useful for prognosis. The term 'prognosis', herein relates to methods for predicting the outcome of pathology or for predicting the probability or likeliness that an adverse outcome will be observed in a patient.

It is desirable to identify a sensitive, cardiac specific and early detectable marker which bears a close relation to the extent of cardiac problem/damage and which provides prognostic information. Therefore, there is need for reliable methods, apparatuses and biomarkers for early diagnosis or detection of acute coronary syndrome and reliable methods for predicting adverse cardiac events in a setting of acute coronary syndrome.

SUMMARY OF THE INVENTION

The invention provides a method for detecting acute coronary syndrome in a human subject by obtaining a test sample from the biological fluid of the human subject, analyzing the test sample for amount of catalytic iron and detecting acute coronary syndrome in the human subject. The biological fluid is selected from a group comprising blood, serum and plasma. In an embodiment, the step of analyzing comprises comparing the amount of catalytic iron with a predetermined amount. In an embodiment, the test sample is obtained within about first three hours after the onset of a chest pain in the human subject or whenever the human subject (patient) suspected of heart disease is available for the test.

In an embodiment, the invention provides a method for detecting acute coronary syndrome in a human subject by analyzing a test sample obtained from the biological fluid of the human subject for amount of Bleomycin detectable iron. The acute coronary syndrome may be detected on the basis of results of the comparison of amount of Bleomycin detectable iron with a predefined amount. The biological fluid is selected from a group comprising blood, serum and plasma. The invention provides a method for predicting adverse cardiac outcomes for a human subject having acute coronary syndrome by analyzing an increase in levels of Bleomycin detectable iron in the test sample obtained at a predetermined time.

In an embodiment the invention provides a method for detecting acute coronary syndrome in a human subject at the time of presentation of the chest pain including obtaining a test sample from the biological fluid of the human subject and analyzing the test sample for amount of catalytic iron wherein the human subject is presented after the onset of chest pain. The acute coronary syndrome may be detected on the basis of results of the comparison of amount of catalytic iron with a predefined amount. The biological fluid is selected from a group comprising blood, serum and plasma. According to an exemplary embodiment, the human subject is presented within about first three hours after the onset of chest pain. In an embodiment the invention provides a method for early detection of the acute coronary syndrome including obtaining a test sample from the biological fluid of the human subject and analyzing the test sample for amount of catalytic iron wherein the human subject is presented early after the onset of chest pain.

In another embodiment the invention provides a method for predicting adverse cardiac outcomes for a human subject having acute coronary syndrome comprising obtaining a first test sample from the biological fluid of a human subject at a first time point at the time of presentation after chest pain, analyzing the first test sample for amount of catalytic iron; detecting acute coronary syndrome in the human subject; obtaining a second test sample from the biological fluid of a human subject after a predefined time interval from the first time point, suitable to observe a consequential variation or increase in the levels of Bleomycin detectable iron. The 'consequential increase' in this document refers to an elevation in the levels of the catalytic iron (e.g. Bleomycin detectable iron), sufficient to provide prognostic information useful for predicting the adverse outcomes. The method further comprising analyzing the second test sample for amount of catalytic iron and measuring the increase in the amount of catalytic iron in second sample compared to the first sample. One or more adverse cardiac outcome(s) may be predicted on the basis of analyzing the second test sample. The biological fluid is selected from a group comprising blood, serum and plasma. According to an exemplary embodiment, the test sample is obtained after a predefined time interval from the detection of acute coronary syndrome, the predefined time interval being suitable to observe a consequential variation or increase in the levels of catalytic iron. According to an exemplary embodiment the test sample is obtained after about 24 hours of detecting acute coronary syndrome in the human subject.

In yet another embodiment, the invention provides a method for predicting adverse cardiac outcomes for a human subject having acute coronary syndrome comprising obtaining a test sample from the biological fluid of a human subject and analyzing the test sample for amount of catalytic iron for predicting one or more adverse cardiac outcome(s) on the basis of analyzing the test sample. The test sample is obtained after a predefined time interval suitable to observe a consequential variation or increase in the levels of catalytic iron. The biological fluid is selected from a group comprising blood, serum and plasma. According to an exemplary embodiment, the test sample is obtained after a predefined time interval from the detection of acute coronary syndrome, the predefined time interval being suitable to observe a consequential variation or increase in the levels of catalytic iron. According to an exemplary embodiment the test sample is obtained after about 24 hours of detecting acute coronary syndrome in the human subject.

According to a still another embodiment steps of obtaining the test sample and analyzing it for amount catalytic iron are repeated for obtaining a data set corresponding to an increase in the levels of catalytic iron and on the basis of the analysis of the dataset, one or more adverse cardiac outcome(s) is/are predicted. According to an exemplary embodiment the predicted adverse cardiac outcomes are selected from one or more of heart failure, worsening heart failure, reinfarction, stent thrombosis and death.

In an embodiment, the invention provides a method for treating a human subject suffering from acute coronary syndrome by analyzing a test sample obtained from the biological fluid of the human subject for amount of catalytic iron, the biological fluid is selected from a group comprising blood, serum and plasma, detecting acute coronary syndrome on the basis of results of the comparison of amount of catalytic iron with a predefined amount and administering a therapeutically effective amount of an iron chelating agent. According to an exemplary embodiment, a therapeutically effective amount of an iron chelating agent is administered after predicting the adverse cardiac outcomes on the basis of analyzing the increase in the levels of catalytic iron. The method may further include administering one or more suitable iron chelating agent(s) in a therapeutically effective amount.

According to an embodiment the invention provides a method for differentiating chest pain corresponding to acute coronary syndrome from non-cardiac chest pain in a human subject. The method includes analyzing a test sample for amount of catalytic iron; comparing the amount of catalytic iron with a predetermined amount; and differentiating chest pain corresponding to acute coronary syndrome from non-cardiac chest pain in response to comparing. The test sample is obtained from blood, serum or plasma of the human subject. According to an exemplary embodiment the human subject is presented, within about 0-6 hours of the onset of chest pain.

In an embodiment, the invention provides a kit for detecting acute coronary syndrome in a human subject. The kit includes receptacle means for receiving a test sample from the biological fluid of the human subject, means for analyzing the test sample for amount of catalytic iron and means for detecting acute coronary syndrome in the human subject. The biological fluid is selected from a group comprising blood, serum and plasma. According to an exemplary embodiment the kit enables detecting ACS in a human subject within about 0-6 hours of onset of chest pain.

In an embodiment the invention provides a method for use of a catalytic iron assay for detecting acute coronary syndrome in a human subject by analyzing amount of catalytic iron in a blood, serum or plasma sample of the human subject. In an embodiment, the invention provides a method for use of a Bleomycin-detectable iron assay for detecting acute coronary syndrome in a human subject. The method includes analyzing amount of Bleomycin detectable iron in a test sample obtained from the biological fluid of the human subject. The biological fluid is selected from a group comprising blood, serum and plasma.

In yet another embodiment the invention provides a method for use of a catalytic iron assay for predicting one or more adverse cardiac outcome(s) in a human subject having acute coronary syndrome. The method includes analyzing amount of catalytic iron in a test sample obtained from the biological fluid of the human subject having acute coronary syndrome. According to an exemplary embodiment, the test sample is obtained after a predefined time interval from the detection of acute coronary syndrome, the predefined time interval being suitable to observe a consequential variation or increase in the levels of catalytic iron. The biological fluid is selected from a group comprising blood, serum and plasma.

DETAILED DESCRIPTION OF THE INVENTION

Figure 1:
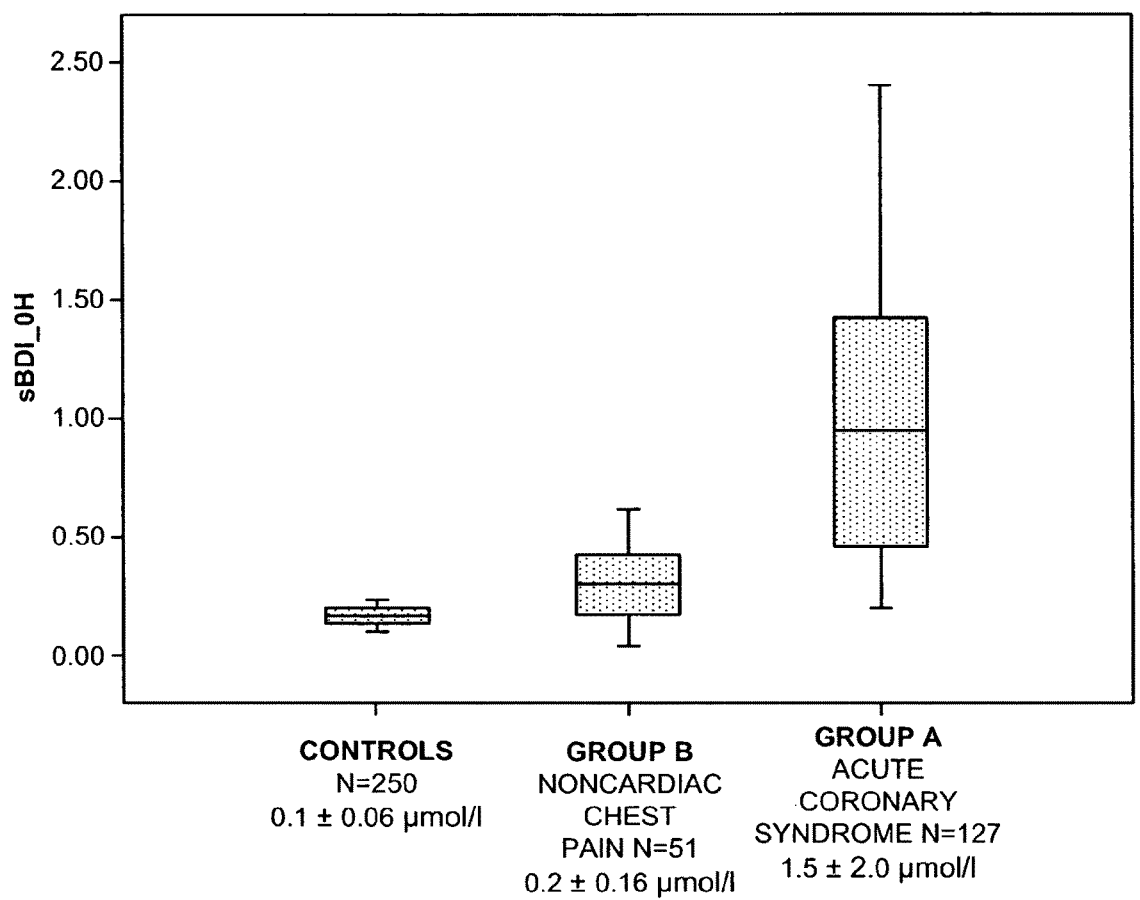
FIG. 1 illustrates box plots showing median levels of serum catalytic iron measured at baseline in the Emergency department in three groups of patients in accordance with the invention, the boxes shows interquartile ranges and the bar represents highest and lowest values.

Various embodiments of the invention are disclosed herein; however, it is to be understood that the disclosed embodiments are merely exemplary of the invention, which can be embodied in various forms. Therefore, specific structural, functional, formulation, process or method details disclosed herein are not to be interpreted as limiting, but merely as a representative basis for teaching one skilled in the art to variously employ the invention in virtually any appropriately detailed method, structure, application, usage, process or formulation. Further, the terms and phrases used herein are not intended to be limiting but rather to provide an understandable description of the invention.

In this document, relational terms such as first and second, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, or apparatus that comprises, has, includes, contains a list of elements/steps does not include only those elements/steps but may include other elements not expressly listed or inherent to such process, method or apparatus. An element/step proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art.

The invention provides a method for detecting acute coronary syndrome in a human subject by obtaining a test sample from the biological fluid of the human subject, analyzing the test sample for amount of catalytic iron and detecting acute coronary syndrome in the human subject. The biological fluid is selected from a group comprising blood, serum and plasma. In an embodiment, the step of analyzing comprises comparing the amount of catalytic iron with a predetermined amount. This relates to the discovery that catalytic iron in the biological fluid such as blood, serum or plasma of a human may be an indicator of the presence of acute coronary syndrome. The invention further relates to the discovery that an increase in the amount of catalytic iron may provide useful prognosis information for predicting adverse cardiac outcomes for the human subject having acute coronary syndrome. Particularly a data set corresponding to serial elevation in the amount of serum catalytic iron enables prediction of adverse cardiac outcomes. It has been found to be a sensitive, cardiac specific and early detectable marker which bears a close relation to the extent of cardiac problem/damage and which provides useful prognostic information for the human subjects having acute coronary syndrome (ACS). A measure of high oxidative stress in the body may be determined by detecting high levels of catalytic iron in the serum in order to detect ACS at an early stage for example by way of using Bleomycin detectable iron assay. Use of this assay also enables a more reliable and early prediction of adverse cardiac outcomes of the ACS. Suitable methods may be used to measure and analyze the variation in the amount of catalytic iron in the biological fluid e.g., serum.

According to an exemplary embodiment the predetermined amount is at least about 0.3 µ mole/L. ACS may be detected in cases where the amount of Bleomycin detectable iron exceeds this limit. If the amount of the catalytic iron is less than about 0.3 µ mole/L then the chest pain may be considered as a non-cardiac chest pain. In an embodiment, the test sample is obtained within about first three hours after the onset of a chest pain in the human subject. The method of the invention enables early diagnosis of the ACS, for example the test sample may be collected anytime after the onset of the chest pain or whenever the patient suspected of heart diseases is available for the test. This makes it very useful for making appropriate therapeutic decisions at an early stage.

In an embodiment, the invention relates to a method for detecting acute coronary syndrome in a human subject by analyzing a test sample obtained from the biological fluid of the human subject for amount of Bleomycin detectable iron. This relates to the discovery that catalytic iron e.g. determined by way of using a Bleomycin detectable iron assay, in the biological fluid such as blood, serum or plasma of a human may be an indicator of the presence of ACS. Plaque rupture and vascular damage happens as a result of high levels of oxidative stress in the body. The oxidative stress is a result of high levels of what are called reactive oxygen species. These include hydroxyl radicals, free oxygen radicals and hydrogen peroxide. A very strong catalyst for the production of these reactive oxygen species is free iron or catalytic iron. Iron in the body is present in the tissues tightly bound to ferretin whereas in the blood iron circulates tightly bound to transferrin. When catalytic iron levels rise, oxidative stress increases leading to vascular damage causing various medical conditions like heart attacks, kidney damage and strokes.

The invention further relates to the discovery that an increase in the amount of Bleomycin detectable iron may provide useful prognosis information for predicting adverse cardiac outcomes for the human subject having acute coronary syndrome. Particularly a data set corresponding to serial elevation in the amount of serum Bleomycin detectable iron enables prediction of adverse cardiac outcomes. It has been found to be a sensitive, cardiac specific and early detectable marker which bears a close relation to the extent of cardiac problem/damage and which provides useful prognostic information for the human subjects having ACS. A measure of high oxidative stress in the body may be determined by detecting high levels of catalytic iron in the serum in order to detect ACS at an early stage e.g. by way of using Bleomycin detectable iron assay. Use of this assay also enables a more reliable and early prediction of adverse cardiac outcomes of the ACS.

The 'test sample' refers to blood-based samples, such as whole-blood samples, serum or plasma samples. The level of a marker may be determined once or repeatedly at a predefined time interval. The term 'detecting'/diagnosing or 'detection'/diagnosis along with ACS refers to confirming the presence of ACS or heart disease in response to analyzing the test sample for the amount of catalytic iron. These terms may also refer to the establishment of a non-cardiac chest pain in cases where the amount of catalytic iron measured is less than a predetermined amount. In a preferred embodiment the test sample is a serum sample. An acute coronary syndrome (ACS) refers to a set of signs and symptoms, usually a combination of chest pain and other features, interpreted as being the result of abruptly decreased blood flow to the heart (cardiac ischemia). The most common cause for this is the disruption of atherosclerotic plaque in an epicardial coronary artery. The subtypes of acute coronary syndrome include unstable angina (UA), and two forms of myocardial infarction (heart attack), in which heart muscle is damaged. The term 'human subject' (or 'patient') refers to a person with the complaint of chest pain and/or of suspected heart disease. 'Catalytic iron' refers to chemical forms of iron that can participate in redox cycling. This property makes iron potentially hazardous in that it enables it to participate in the generation of powerful oxidant species such as hydroxyl radical (see metal-catalyzed Haber-Weiss reaction formula) and/or reactive iron-oxygen complexes such as ferryl or perferryl ion.

$$Fe^{3+} + O_2\bullet \longrightarrow Fe^{2+} + O_2$$
$$Fe^{2+} + H_2O_2 \longrightarrow Fe^{3+} + OH^- + OH\bullet$$
$$O_2 + H_2O_2 \longrightarrow O_2 + OH^- + OH\bullet$$

Although human body contains as much as 3-5 g of total iron, the pool of catalytic iron is estimated to be <70-90 mg. We now recognize that this pool of catalytic iron is increased in many disease states. Several methods have been described to measure catalytic iron, also referred to as labile iron or toxic iron (Halliwell B, Gutteridge J M C. Role of free radicals and catalytic metal ions in human disease: an overview. Meth Enzymol 1990; 186: 1-85 and Kakhlon O, Cabantchik Z I. The labile iron pool: characterization, measurement, and participation in cellular processes. Free Rad Biol Med 2002; 33: 1037-1046.)

Reactive oxygen species (ROS) have been researched extensively and are believed to be responsible for various forms of vascular (blood vessel) damages. ROS (e.g. hydroxyl ion, superoxides etc) are extremely difficult to measure since they are highly unstable and reactive. The production of these ROS in the body is catalyzed by labile iron or catalytic iron. Measuring the levels of catalytic iron therefore provides with an indirect measure of the level of ROS present at that time in the body.

Measurement of catalytic iron in serum has been described in literature e.g. a test described by Gutteridge J M C et al titled "Superoxide dependent formation of hydroxyl radicals and lipid peroxidation in the presence of iron salts. Detection of 'catalytic' iron and anti-oxidant activity in extracellular fluids" (Biochem J 1982; 206: 605-609). The test briefly detects catalytic iron by its ability to degrade DNA in the presence of Bleomycin which is a commonly used anticancer drug. However, the sensitive nature of the test poses some important challenges to measure the correct levels of catalytic iron e.g. by way of avoiding situations and/or conditions which give rise to falsely high levels of catalytic iron. In a preferred embodiment, Bleomycin detectable iron assay is used for the purpose of detecting ACS and predicting adverse cardiac outcomes.

In an embodiment, the invention provides a method for detecting acute coronary syndrome in a human subject by analyzing a test sample obtained from the biological fluid of the human subject for amount of Bleomycin detectable iron. The acute coronary syndrome may be detected on the basis of results of the comparison of amount of Bleomycin detectable iron with a predefined amount. The biological fluid is selected from a group comprising blood, serum and plasma. The invention provides a method for predicting adverse cardiac outcomes for a human subject having acute coronary syndrome by analyzing an increase in levels of Bleomycin detectable iron in the test sample obtained at a predetermined time. According to an embodiment of the invention, Serum Bleomycin detectable catalytic iron is measured by following a method based on the formation of a Bleomycin-iron complex, which reacts with DNA resulting in its degradation. According to an embodiment of the invention, DNA degradation products, viz. malondialdehyde were measured by known methods, for example DNA degradation products, viz. malondialdehyde were measured by thiobarbituric acid reaction an assay described by Evans and Halliwell. In an embodiment of the invention a method described by Gutteridge J M C et al titled "Superoxide dependent formation of hydroxyl radicals and lipid peroxidation in the presence of iron salts. Detection of 'catalytic' iron and anti-oxidant activity in extracellular fluids" is used. (Biochem J 1982; 206: 605-609)

According to an exemplary embodiment of the invention, the predetermined amount is at least about 0.3 μ mole/L. Thus, ACS may be detected in cases where the amount of Bleomycin detectable iron exceeds this limit. According to an exemplary embodiment of the invention, the test sample is obtained within about first three hours of the onset of the chest pain in the human subject. The enables early detection of ACS e.g. within first three hours of onset of chest pain, which makes it very useful for making appropriate therapeutic decisions early.

In an embodiment of the invention, the human subject presents a chest pain. In another embodiment of the invention, the human subject presents a normal cardiac Troponin level. In an embodiment, the human subject presents a normal cardiac Troponin level and/or a normal CK level. In another embodiment of the invention, the human subject presents a normal cardiac Troponin I or cardiac Troponin T level. In a yet another embodiment, the human subject presents a normal cardiac Troponin I or cardiac Troponin T level and indicating no elevation of the ST segment. The methods of the invention enable diagnosing ACS and predicting adverse outcomes in all the above categories of patients with considerable precision.

An embodiment of the invention provides a method for early diagnosis or detection of ACS in a human subject at the time of presentation of the chest pain comprising the steps of obtaining a test sample from the biological fluid (such as blood, serum or plasma) of the human subject; analyzing the test sample for amount of Bleomycin detectable iron and detecting ACS in the human subject.

An embodiment of the invention provides a method for early detection of acute coronary syndrome in a human subject at the time of presentation of the chest pain comprising the steps of obtaining a test sample from the biological fluid (such as blood, serum or plasma) of the subject; analyzing the test sample for amount of Bleomycin detectable iron and detecting acute coronary syndrome in the human subject, wherein the human subject is presented, within about first 3 hours of the onset of chest pain.

In an exemplary embodiment of the invention, a strict neutral pH is maintained during the process of implementing the method using Bleomycin-detectable iron assay, for example for implementing the method suggested by Gutteridge J M C et al titled "Superoxide dependent formation of hydroxyl radicals and lipid peroxidation in the presence of iron salts. Detection of 'catalytic' iron and anti-oxidant activity in extracellular fluids" (Biochem J 1982; 206: 605-609). The strict maintenance of pH enables prevention or reduction of the possibility of indicating falsely high levels of catalytic iron and thus unreliable detection of ACS for a human subject with chest pain. According to an embodiment of the invention, the entire assay has to be done in strictly iron free environment. According to an exemplary embodiment of the invention, all solutions are freshly prepared and treated with suitable reagents such as chelex powder to extract any iron impurities present in the solution.

An embodiment of the invention provides a method for predicting adverse cardiac outcomes for a human subject comprising: obtaining a first test sample from the biological fluid (such as blood, serum or plasma) of a human subject at a first time point; analyzing the first test sample for amount of catalytic iron; detecting acute coronary syndrome in the human subject; obtaining a second test sample from the biological fluid of a human subject after a predefined time interval from the first time point, the predefined time interval being suitable to observe a consequential variation or increase in the levels of catalytic iron; analyzing the second test sample for amount of catalytic iron; predicting one or more adverse cardiac event(s)/outcome(s) on the basis of analyzing the second test sample. In a preferred embodiment, the method comprises measuring the amount of Bleomycin detectable iron in order to detect ACS and predict adverse cardiac outcomes.

According to an exemplary embodiment, the second test sample is taken in response to detection of acute coronary syndrome in the human subject. Serial elevations of catalytic iron predict higher complication rate. According to an exemplary embodiment of the invention, the method for predicting adverse cardiac outcomes for a human subject comprises predicating the presence of one or more adverse cardiac events selected from new or worsening heart failure, cardiogenic shock, reinfarction, stent thrombosis and death in response to determining significant increase in the levels of serum catalytic iron e.g. Serum Bleomycin Detectable Iron from baseline to about 24 hours after presentation. Adverse cardiac outcomes including new or worsening heart failure, cardiogenic shock, reinfarction, stent thrombosis and death was strongly correlated to significant increases in the levels of Serum Bleomycin Detectable Catalytic Iron from baseline to 24 hours after presentation. No such correlation was observed between adverse cardiac outcomes and serial estimations of biomarker such as troponin I. Details of an exemplary study are provided in the example section of this document.

In an embodiment, the invention provides a method for treating a human subject suffering from ACS including obtaining a first test sample from the biological fluid (such as blood, serum or plasma) of the human subject at a first time point; analyzing the first test sample for amount of catalytic iron; detecting acute coronary syndrome in the human subject; obtaining a second test sample from the biological fluid (such as blood, serum or plasma) of a human subject after a predefined time interval from the first time point, the predefined time interval being suitable to observe a consequential variation or increase in the levels of catalytic iron; analyzing the second test sample for amount of catalytic iron; predicting one or more adverse cardiac outcome(s) on the basis of analyzing the second test sample and administering a therapeutically effective amount of one or more iron chelating agent(s). According to an embodiment of the invention, the first test sample is obtained within about first 3-6 hours of onset of chest pain of the human subject and the second test sample is obtained after about 20-30 hours of onset of chest pain of the human subject. The test may be conducted at the time of presentation of the chest pain. According to an embodiment, serial elevation may be observed at a suitable frequency in order to predict the adverse cardiac event(s)/outcome(s). The suitable frequency may be determined on the basis of e.g. examination and detected levels of serum catalytic iron. In an embodiment, iron chelating agent(s) may be administered after detecting ACS in the human subject. In an embodiment the method of treating the human subject suffering from ACS includes predicting adverse cardiac outcomes in accordance with the method(s) of the invention and administering a suitable iron chelating agent(s).

In an embodiment of the invention, the iron chelating agent is selected from the group comprising one or more of deferipone, desferrioxamine, rhodotorulic acid, and 2, 3-dihydroxybenzoic acid or physiologically acceptable salt thereof. Any suitable known or developed chelating agent or their suitable combinations may be used or after early detection of ACS for the treatment.

According to an embodiment of the invention, the first test sample is obtained within about 3 hours of onset of chest pain of the human subject and the second test sample is obtained after about 24 hours of onset of chest pain of the human subject. According to an embodiment of the invention, the test sample may be collected from the serum of any human subject suspected of suffering from the heart disease or ACS. The test sample may be collected from the serum of a human subject complaining of chest pains. In an embodiment the invention provides a method of use of serum Bleomycin detectable iron for early diagnosis or early detection of acute coronary syndrome in a human subject.

In an embodiment the invention provides a method for use of a catalytic iron assay for detecting acute coronary syndrome in a human subject by analyzing amount of catalytic iron in a blood, serum or plasma sample of the human subject. In an embodiment, the invention provides a method for use of a Bleomycin detectable iron assay for detecting acute coronary syndrome in a human subject by analyzing amount of catalytic iron in a blood, serum or plasma sample of the human subject.

In an embodiment the invention provides a method of use of Bleomycin detectable iron for a prediction of adverse cardiac events/outcomes in a human subject. The use of serum Bleomycin detectable iron as a biomarker enables more reliable prediction of adverse cardiac events and thus facilitates the physician to take better decisions for treatment/therapy of the condition.

In an embodiment, the invention provides a method for use of a catalytic iron (e.g. Bleomycin detectable iron) assay for differentiating chest pain corresponding to acute coronary syndrome from non-cardiac chest pain in a human subject by analyzing amount of Bleomycin detectable iron in blood, serum or plasma sample of the human subject.

In an embodiment the invention provides a method for use of a catalytic iron (e.g. Bleomycin detectable iron) assay for predicting one or more adverse cardiac outcome(s) in a human subject having acute coronary syndrome, by analyzing amount of catalytic iron in the blood, serum or plasma sample of the human subject. In an embodiment the invention provides the use of a catalytic iron assay wherein said blood, serum or plasma sample is derived from a blood sample taken from the human subject after a predefined time interval from the detection of acute coronary syndrome. The predefined time interval is suitable to observe a consequential variation or increase in the levels of catalytic iron. For example the time interval is 20-24 hours after the detection of ACS.

An embodiment of the invention provides a kit for early diagnosis or detection of acute coronary syndrome (ACS) in human subject at the time of presentation of the chest pain. The kit enables estimation of catalytic iron as a biomarker in order to detect and correctly differentiate cardiac pain from non-cardiac chest pain (e.g. muscular pain) at the time of presentation of the patient. The other use of the kit is to identify patients who are likely to get into complications during their hospitalization including death and recurrence of pain. In an embodiment, the invention provides a kit for early diagnosis (e.g. within at least about 0-6 hours) or detection of acute coronary syndrome comprising means (e.g. receptacle means) for obtaining a test sample from the biological fluid (such as blood, serum or plasma) of the human subject, means for analyzing the test sample for amount of catalytic iron and means for analyzing and detecting acute coronary syndrome in the human subject. In an exemplary embodiment, the kit enables the implementation of a Bleomycin detectable iron assay for detecting the ACS and predicting adverse cardiac outcomes.

According to an embodiment, the above described method for detecting ACS and method for predicting adverse cardiac outcomes for a human subject having ACS from the measured level(s)/amount(s) of the catalytic iron (e.g. Bleomycin detectable iron), are performed by a computer implemented system. Appropriate therapeutically decisions regarding e.g. hospitalization or treatment are taken by the practitioner using the method(s) according to the invention.

In the foregoing disclosure, exemplary embodiments of the invention have been described. However, one of ordinary skill in the art appreciates that various modifications and changes may be made without departing from the scope of the invention. Accordingly, the complete specification is to be regarded in an illustrative rather than a restrictive sense, and all such modifications are intended to be included within the scope of the invention. The benefits, advantages, solutions to problems, and any element(s)/feature(s)/step(s)/usage/application that may cause any benefit, advantage, or solution to occur or become more pronounced are not to be construed as a critical, required, or essential features or elements with reference to the disclosure.

EXAMPLE

The examples and experiments are presented solely for the purpose of illustration and should not be construed as limiting the invention.

Study Population

A total of 178 human patients were enrolled in these studies who presented with acute chest pain to the emergency department between April 2006 to October 2007. Patient's detailed clinical history and physical examination was recorded. A resting electrocardiogram was obtained and analyzed for ST segment shifts and ischemic changes. Echocardiograms were obtained either in the emergency department or on transfer to the cardiac care units. Blood sampling for cardiac biomarkers including troponin I and Serum Bleomycin Detectable Catalytic Iron was done at the time of presentation and at 12 and 24 hours after admission to cardiac care unit. All patients then underwent standard cardiac care depending on the clinical condition at the time of presentation. All patients were followed for at least 30 days and adverse events recorded for death, new or worsening heart failure, cardiogenic shock, reinfarction and stent thrombosis.

For the sake of comparisons, 250 normal asymptomatic volunteers with no major medical history who were age matched with the patients with chest pain were studied as controls.

Blood Sampling

At the time of enrollment, 10 ml blood sample was collected in plain tube. The serum component was frozen and transported on dry ice to a testing site where the samples were stored at $-70°$ C. All the samples were then thawed at the time of analysis.

Biochemical Analysis

Troponin I was measured using the immunoenzymometric assay using the kit provided by Calbiotech Inc USA (Product number: TI015CM)

Serum Bleomycin detectable catalytic iron was measured by following a method based on the formation of a Bleomycin-iron complex, which reacts with DNA resulting in its degradation. DNA degradation products, viz, malondialdehyde were measured by thiobarbituric acid reaction an assay described by Evans and Halliwell. The reactions were carried out in one-half the recommended volume and performed in disposable polypropylene tube to avoid the iron contamination from external sources. All the reagent solutions, except the Bleomycin, were treated overnight with chelex (300 mg for 10 ml solution) to remove any excess iron in the chemicals.

The assay mixture was prepared as follows: 250 µ mole/L 1 mg/ml DNA solution (calf thymus DNA-type I, Sigma D1501), 25 µl of 1.5 KIU/L Bleomycin sulfate (Sigma B5507), 50 µl of 50 µ mole/L $MgCl_2$ (Sigma M2670), 25 µl of sample, standard or blank and 50 µl of 8 µmole/L ascorbic acid (Sigma A1417). The pH of all standards, samples and their blanks were adjusted to 7.4 using a predetermined volume of 40 µmole/L of either HCl or NaOH (Sigma S8045) solutions. The tubes containing the assay components were then incubated at 370 C water bath at a slow shaking condition for 2 hrs. The reaction was stopped by the addition of 50 µl of 0.1 µmole/L of EDTA (Sigma E9884) solution in all the tubes. Added 500 µl of Thiobarbituric acid (TBA) (Sigma T5500) (1% w/v, in 50 µmole/L NaOH) and 500 µl of 25% HCl (J. T. Baker UN 1789) in them. The tubes were then incubated in a 1000° C. water bath for 15 minutes. The reaction tubes were then cooled down at room temperature. The tubes containing the colored products were then centrifuged at 1500 g for 10 minutes to isolate the precipitated protein in the supernatant. The intensity of the color was then measured in a spectrophotometer (Cyber UV-1, Mecasys Co. Ltd. Korea) at 532 nm against blank (without Bleomycin).

A standard graph was prepared, fresh with each batch of assay, using $FeCl_3$ (Sigma F7134) with standard iron concentrations ranging from 0.1-1000 µ mole/L. The 3-cycle logarithmic-logistic plot of the optical density of the color of the iron standard against the corresponding concentrations was used for the estimation of serum Bleomycin detectable iron in unknown samples.

Statistical Analysis

Patients were divided in two groups. Group A having acute coronary syndrome and Group B having noncardiac chest pain. The controls were 250 asymptomatic volunteers having no major medical history. Comparisons of Serum Bleomycin Detectable Catalytic Iron and troponin I values in various groups were performed by the t-test for independent samples and analysis of variance. Log-transformed values for Serum Bleomycin Detectable Catalytic Iron and troponin I were used to reduce effects of skewness in the distribution.

To evaluate the role of Serum Bleomycin Detectable Catalytic Iron measurements in the diagnosis of acute coronary syndrome, the sensitivity, specificity and accuracy of Serum Bleomycin Detectable Catalytic Iron measurements were compared within the different groups. Finally, receiver-operating-characteristic curves were constructed to illustrate various cutoff values of Serum Bleomycin Detectable Catalytic Iron.

Results

The baseline characteristics and risk factor profiles of the groups studied are shown in Table 1. Out of the 178 patients who presented to the emergency department with acute chest pain, 127 patients were diagnosed to have an ACS based on the electrocardiogram and serial cardiac troponin I estimations. 51 patients had nonspecific ECG changes with negative troponin I and underwent subsequent non invasive testing to confirm that their chest pain was non-cardiac in origin. These two groups A & B were compared with 250 normal asymptomatic volunteers who were age matched.

Amongst patients with acute coronary syndrome, 61 (48.0%) patients presented within 3 hours of the onset of chest pain, 43 (33.9%) patients presented 4-12 hours after the onset of symptoms and 23 (18.1 %) presented more than 12 hours after symptom onset. 63 (49.6%) patients at the time of presentation had ECG evidence of ST elevation myocardial infarction, 64 (50.4%) patients had significant ST segment depression (>1 mm) and were troponin I positive on serial estimations.

Box plots of the baseline Serum Bleomycin Detectable Catalytic Iron measurements in all three groups are shown in FIG. 1. There was highly statistically significant difference between patients with ACS and controls (p<0.0001*). The difference between acute coronary syndrome and non-cardiac chest pain was also significant (p<0.0001*). Controls had a mean (+SEM) Serum Bleomycin Detectable Catalytic Iron level of 0.1+0.06 µmole/L which is similar to the previously published data on normal healthy volunteers. Patients with non-cardiac chest pain had Serum Bleomycin Detectable Catalytic Iron levels of 0.26+0.16 µmole/L. Patients with acute coronary syndrome had a mean baseline Serum Bleomycin Detectable Catalytic Iron of 1.55+2.02 µmole/L irrespective of the time from symptom onset to clinical presentation to the emergency department.

Figure 2:
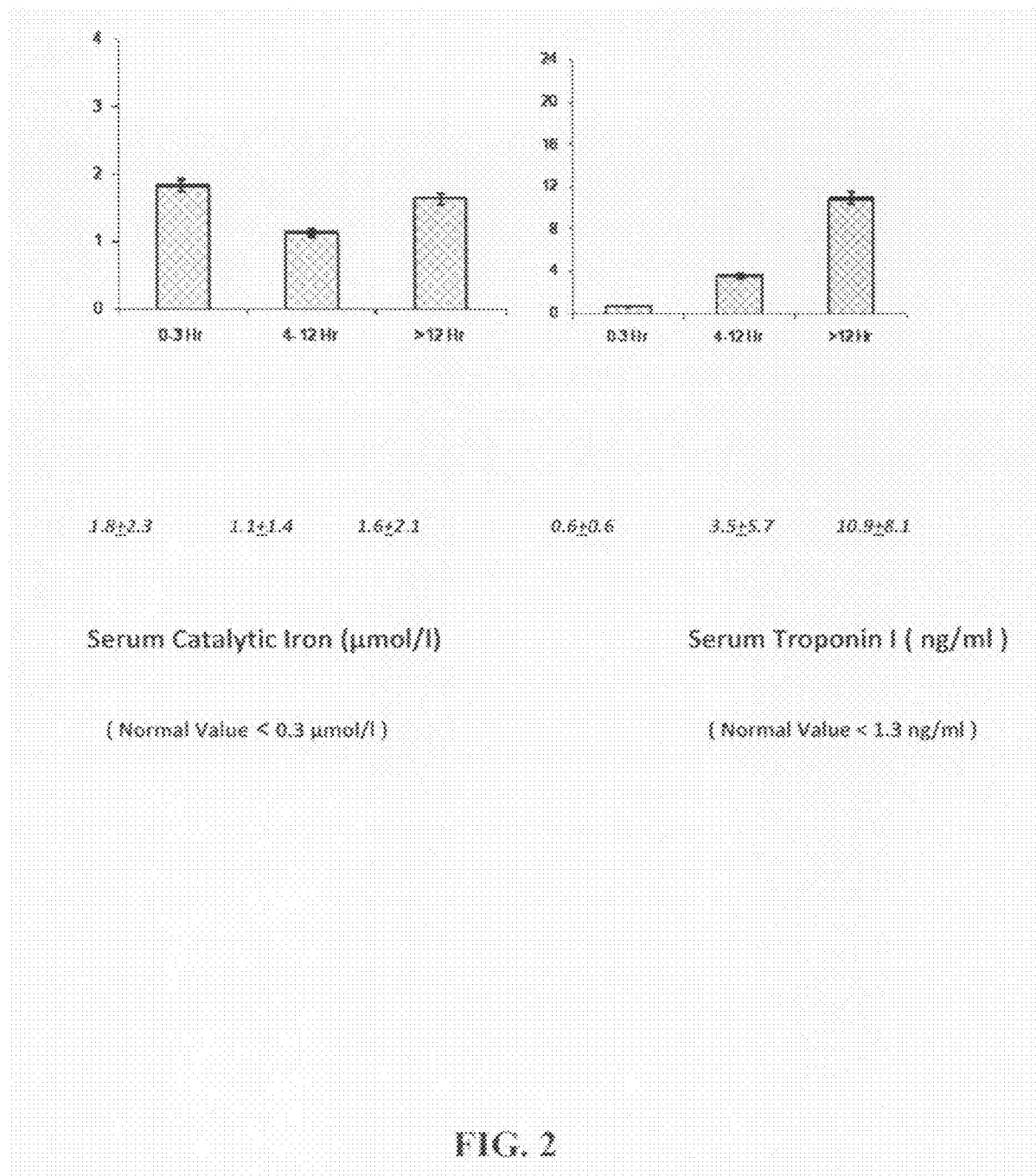
FIG. 2 illustrates Serum Catalytic Iron and Troponin I measured at baseline and at the time of presentation in three groups divided by the time of symptom onset to presentation in emergency department.

Patients of acute coronary syndrome who presented within 3 hours (FIG. 2) after the onset of chest pain had a mean baseline sBDI of 1.82+1.71 µmole/L. This was significantly higher than both controls and those with non-cardiac chest pain. The baseline troponin I level among these subset of patients was 0.6+0.8 pg/l which was well within the levels of normality and thus failed to detect patients with acute coronary syndrome. Serial troponin I estimations in this subset showed a significant rise when measured 24 hours after presentation confirming that these patients had acute coronary syndrome.

Figure 3:
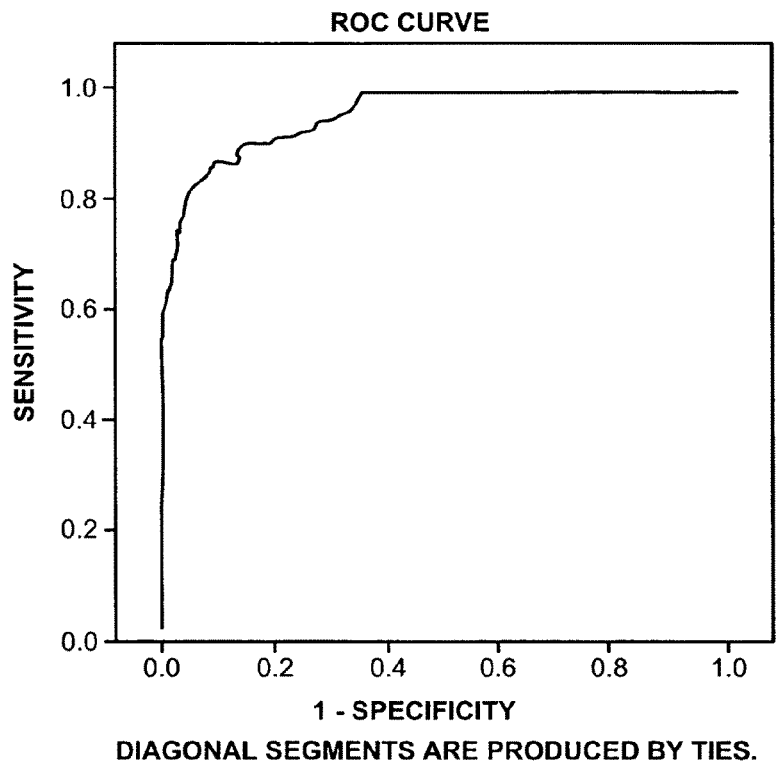
FIG. 3 illustrates Receiver-Operating-Characteristic Curve for various cutoff levels of Serum Catalytic Iron in Differentiating between chest-pain due to an acute coronary syndrome from non-cardiac chest pain in accordance with the invention.

Serum Bleomycin Detectable Catalytic Iron at baseline was the single most accurate predictor of high risk acute coronary syndrome in patients presenting with chest pain to the emergency department. The ability of Serum Bleomycin Detectable Catalytic Iron measurement to differentiate cardiac from non-cardiac chest pain was assessed using a receptor-operating characteristic curve analysis FIG. 3. The area under the curve was used to differentiate acute coronary syndrome from non-cardiac chest pain with a diagnostic accuracy of 92% at a cutoff sBDI level of 0.3 µmole/L. At this level the negative predictive value of the test was 93% and a specificity of 95%.

Figure 4:
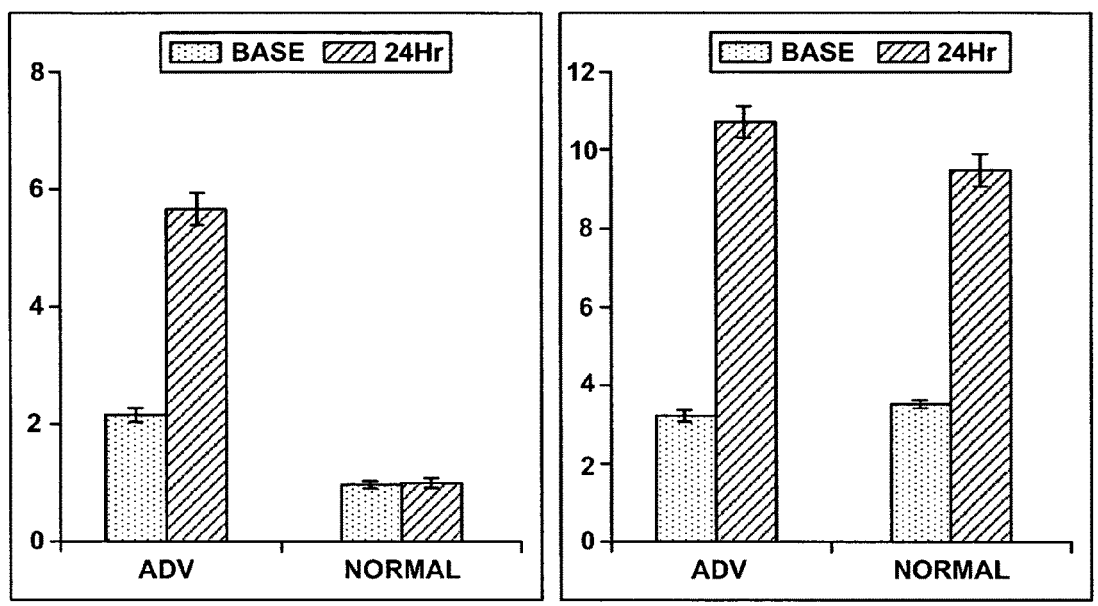
FIG. 4 illustrates association between Serial Catalytic Iron estimations and Serial Troponin I estimations and adverse cardiac events in accordance with the invention. (e.g. New or worsening heart failure, cardiogenic shock, reinfarction, Stent thrombosis and mortality)

Adverse cardiac outcomes including new or worsening heart failure, cardiogenic shock, reinfarction, stent thrombosis and death was strongly correlated to significant increases in the levels of Serum Bleomycin Detectable Catalytic Iron from baseline to 24 hours after presentation. No such correlation was observed between adverse cardiac outcomes and serial estimations of troponin I. FIG. 4. On multivariate analysis serial elevation of Serum Bleomycin Detectable Catalytic Iron at 24 hours from baseline was the only significant predictor of adverse cardiac outcomes in patients with acute coronary syndrome (p<0.02 and odds ratio of 1.20) Table 2.

Discussion

The example demonstrates that Serum Bleomycin Detectable Catalytic Iron measurement at the time of presentation of chest pain provides accurate information to identify high risk patients with acute coronary syndrome, as early as within 3 hours of the onset of chest pain. Despite heterogeneity in clinical presentation and risk factor profile, high levels of Serum Bleomycin Detectable Catalytic Iron at baseline was uniformly predictive in identifying patients with high risk acute coronary syndrome who would benefit from therapies such as early antiplatelet, reperfusion and revascularization. This was in contrast to Troponin I measurement which failed to isolate the high risk patients who presented to the emergency department within 3 hours after the onset of the chest pain. Normal baseline Serum Bleomycin Detectable Catalytic Iron catalytic iron estimates also accurately identified the low risk noncardiac chest pain patients.

Increase in Serum Bleomycin Detectable Catalytic Iron at 24 hours from baseline value was predictive of an increased risk of adverse cardiac events defined as new or worsening heart failure, cardiogenic shock, reinfarction, stent thrombosis and mortality in patients with acute coronary syndrome and this relationship was independent of troponin I levels. Various biomarkers have been used to predict adverse cardiac outcomes in patients presenting with acute coronary syndrome. B type natriuretic peptide measured in the first few days after an acute coronary event accurately predicts death and nonfatal events across the entire spectrum of acute coronary syndrome. The study was able to identify a strong correlation between serial elevations in sBDI measurement and 30 day adverse cardiac events.

TABLE 1

Baseline Clinical Characteristics of the three groups studied, clinical features and adverse cardiac outcomes in group with acute coronary syndrome.

| Characteristics | Group A | Group B | Controls |
| --- | --- | --- | --- |
| No of Patients | 127 | 51 | 250 |
| Age (Years) | 59.1 ± 10.8 | 51.7 ± 12.9 | 51.1 ± 10.4 |
| Male Sex (%) | 78 | 51 | 82 |
| Medical History | | | |
| No (%) | | | |
| Hypertension | 79 (62) | 19 (38) | 25 (10) |
| Diabetes | 58 (46) | 12 (24) | 16 (7) |
| Smoking | 23 (18) | 13 (25) | 21 (8) |

TABLE 1-continued

Baseline Clinical Characteristics of the three groups studied, clinical features and adverse cardiac outcomes in group with acute coronary syndrome.

| Characteristics | Group A | Group B | Controls |
|---|---|---|---|
| Hyperlipidemia | 65 (51) | 16 (30) | 85 (34) |
| Systolic Blood Pressure | 119.8 ± 22.5 | 139.1 ± 28.3 | 130.4 ± 15.6 |
| ST Elevation MI | 63 (49) | NA | NA |
| Non ST Elevation MI | 64 (51) | NA | NA |
| EF % | 43 ± 18 | 56 ± 5 | NA |
| Time to Presentation | | | |
| Less than 3 hrs | 61 (41) | NA | NA |
| 4 to 12 hrs | 43 (34) | NA | NA |
| More than 12 hrs | 23 (18) | NA | NA |
| Adverse Cardiac Events | | | |
| Mortality | 8 | NA | NA |
| Reinfarction | 16 | NA | NA |
| Stentthrombosis | 8 | NA | NA |
| Heartfailure | 17 | NA | NA |
| Combined | 17 | NA | NA |

Note:
NA = Not applicable,
Numbers in parenthesis are percentages
Group A = Acute coronary syndrome;
Group B = Non cardiac chest pain

TABLE 2

Multiple Logistical Regression Analysis for Predictors of Adverse Cardiac Outcomes in patients with Acute Coronary Syndrome.

| Predictor | p value | Odds Ratio (95% CI)* |
|---|---|---|
| Age | 0.91 | 1.00 (0.94-1.06) |
| Diabetes | 0.23 | 0.48 (0.15-1.60) |
| Heart Failure | 0.44 | 0.49 (0.78-3.06) |
| Ejection Fraction | 0.97 | 1.00 (0.92-1.09) |
| ST Elevation on ECG | 0.44 | 0.62 (0.18-2.08) |
| SBP at Baseline | 0.54 | 1.00 (0.98-1.03) |
| Change in Troponin I | 0.60 | 1.01 (0.96-1.07) |
| Change in sBDI | 0.02 | 1.20 (1.03-1.40) |

*The odds ratio reflects the odds for patients with the characteristic in question as compared to those without the characteristic. The odds ratio for age represents the exponent for each year of age in the logistic equation. CI denotes confidence interval.

What is claimed is:

1. A method for detecting acute coronary syndrome in a human subject comprising the steps of:
obtaining a test sample from the biological fluid of the human subject, wherein the biological fluid is selected from a group comprising whole blood, serum and plasma;
analyzing the test sample for amount of catalytic iron, wherein the step of analyzing comprises comparing the amount of catalytic iron with a predetermined amount, and wherein the predetermined amount is at least about 0.3 μ mole/L; and
detecting acute coronary syndrome in the human subject based on the analysis of the test sample for the amount of catalytic iron.

2. The method as claimed in claim 1, wherein the test sample is obtained within about six hours after the onset of chest pain in the human subject.

3. A method for detecting acute coronary syndrome in a human subject comprising the steps of:
obtaining a test sample from the biological fluid of the human subject, wherein the biological fluid is selected from a group comprising whole blood, serum and plasma;
analyzing the test sample for amount of bleomycin-detectable iron, wherein the step of analyzing comprises comparing the amount of bleomycin-detectable iron with a predetermined amount, and wherein the predetermined amount is at least about 0.3 μ mole/L; and detecting acute coronary syndrome in the human subject based on the analysis of the test sample for the amount of bleomycin-detectable iron.

4. The method as claimed in claim 3, wherein the test sample is obtained within about six hours after the onset of chest pain in the human subject.

5. A method for differentiating chest pain corresponding to acute coronary syndrome from non-cardiac chest pain in a human subject comprising the steps of:
obtaining a test sample from the biological fluid of the human subject, wherein the biological fluid is selected from a group comprising whole blood, serum and plasma;
analyzing the test sample for amount of catalytic iron comparing the amount of catalytic iron with a predetermined amount, and wherein the predetermined amount is at least about 0.3 μ mole/L; and
differentiating chest pain corresponding to the acute coronary syndrome from the non-cardiac chest pain based on the analysis of the test sample for the amount of catalytic iron.

6. A kit for detecting acute coronary syndrome within about six hours of onset of chest pain in a human subject comprising a receptacle means for receiving a test sample from the biological fluid of the human subject, wherein the biological fluid is selected from a group comprising whole blood, serum and plasma, means for analyzing the test sample for amount of catalytic iron, wherein means for analyzing comprises means for comparing the amount of catalytic iron with a predetermined amount, and wherein the predetermined amount is at least about 0.3 μ mole/L, and means for detecting acute coronary syndrome in the human subject based on the analysis of the test sample for the amount of catalytic iron.

7. The method of claim 1, wherein the step of analyzing comprises comparing the amount of catalytic iron with that of levels of catalytic iron found in a control population.

8. The method of claim 3, wherein the step of analyzing comprises comparing the amount of Bleomycin-detectable iron with that of levels of bleomycin-detectable iron found in a control population.

9. The method of claim 5, wherein the step of analyzing comprises comparing the amount of catalytic iron with that of levels of catalytic iron found in a control population.

* * * * *